United States Patent
Thomas et al.

(10) Patent No.: US 6,759,659 B2
(45) Date of Patent: *Jul. 6, 2004

(54) THERMAL IMAGING SYSTEM FOR DETECTING DEFECTS

(75) Inventors: Robert L. Thomas, Huntington Woods, MI (US); Lawrence D. Favro, Huntington Woods, MI (US); Xiaoyan Han, Plymouth, MI (US); Zhong Ouyang, Glastonbury, CT (US); Hua Sui, Windsor (CA); Gang Sun, Fremont, CA (US)

(73) Assignee: Wayne State University, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/453,081

(22) Filed: Jun. 3, 2003

(65) Prior Publication Data

US 2003/0205671 A1 Nov. 6, 2003

Related U.S. Application Data

(63) Continuation of application No. 09/802,281, filed on Mar. 8, 2001, now Pat. No. 6,593,574, which is a continuation-in-part of application No. 09/397,585, filed on Sep. 16, 1999, now Pat. No. 6,236,049.

(51) Int. Cl.$^7$ .............................................. G01N 29/04
(52) U.S. Cl. ..................................... 250/341.6; 250/334
(58) Field of Search .............................. 250/341.6, 334, 250/332, 330, 347, 341, 338.1, 338.3; 356/381, 237, 502, 498, 482, 432; 374/4, 5, 124, 126, 128, 137; 348/571; 73/620

(56) References Cited

U.S. PATENT DOCUMENTS

| | | | |
|---|---|---|---|
| 3,934,452 A | | 1/1976 | Prevorsek et al. |
| 4,232,554 A | | 11/1980 | Aleck |
| 4,378,701 A | | 4/1983 | Mountain et al. |
| 4,541,059 A | | 9/1985 | Toshihiko |
| 4,607,341 A | | 8/1986 | Monchalin |
| 4,625,557 A | * | 12/1986 | Rutherford .................... 73/635 |
| 4,710,030 A | * | 12/1987 | Tauc et al. ................... 356/432 |
| 4,828,400 A | | 5/1989 | Boyce |
| 4,878,116 A | | 10/1989 | Thomas et al. |
| 4,950,897 A | * | 8/1990 | Mandelis et al. ............ 250/334 |
| 4,950,990 A | | 8/1990 | Moulder et al. |
| 5,201,582 A | | 4/1993 | Lesniak |
| 5,201,841 A | | 4/1993 | Lebeau et al. |
| 5,287,183 A | | 2/1994 | Thomas et al. |
| 5,376,793 A | | 12/1994 | Lesniak |
| 5,417,494 A | | 5/1995 | Kempa et al. |
| 5,476,010 A | * | 12/1995 | Fleming et al. ................ 73/620 |
| 5,495,763 A | | 3/1996 | Rhodes et al. |
| 5,837,896 A | | 11/1998 | Rhodes et al. |
| 6,236,049 B1 | * | 5/2001 | Thomas et al. ........... 250/341.6 |
| 6,399,948 B1 | | 6/2002 | Thomas et al. |
| 6,437,334 B1 | | 8/2002 | Thomas et al. |
| 6,593,574 B2 | * | 7/2003 | Thomas et al. ........... 250/341.6 |

OTHER PUBLICATIONS

Rantala et al. "Lock–in thermography with mechanical loss angle heating at ultrasonic frequencies", QIRT 96, Pisa 1997.*

(List continued on next page.)

Primary Examiner—Constantine Hannaher
Assistant Examiner—Otilia Gabor
(74) Attorney, Agent, or Firm—John A. Miller; Warn, Hoffmann, Miller & LaLone, P.C.

(57) ABSTRACT

A thermal imaging system for detecting cracks and defects in a structure. An ultrasonic transducer is coupled to the structure through a malleable coupler. Ultrasonic energy from the transducer causes the defects to heat up, which is detected by a thermal camera. A control unit is employed to provide timing and control for the operation of the ultrasonic transducer and the camera.

15 Claims, 7 Drawing Sheets

OTHER PUBLICATIONS

Lockin–thermographie, Institut for Kunststoffprufung und Kunststoffkunde/Abteilung Zerstorungsfreie Prufung, Pfaffenwaldring 32 70 569 Stuttgart.

J. Rantala et al., "Lock–in Thermography with mechanical loss angle heating at ultrasonic frequencies", QIRT 98–Eurotherm Series 50–Edizioni ETS, Pisa 1997, pp. 389–393.

E.G. Henneke, and S.S. Russell, Vibrothermography, Nondestructive Testing Handbook Special Nondestructive Testing Methods, vol. 9, Am.Soc. NDT, 1995, pp. 336–340.

Database WPI, Section E1, Week 199328, Derwent Publications Ltd., London, GB: XP–002230464 & SU 1 748 047 A(Orbinsk Tekhnologiya Sci Prodn Assoc), Jul. 15, 1992, abstract.

Database WPI, Section E1, Week 199107, Derwent Publications Ltd., London, GB: XP–002230466 & SU 1 200 675 A (Murata Mfg Co Ltd), Jul. 7, 1990, abstract.

Database WPI, Section E1, Week 198204,, Derwent Publications Ltd., London, GB: XP–002230467 & SU 818 698 A (Mat Non–Dest Test), Apr. 10, 1981, abstract.

R.B. Mignona, R.E. Green, Jr., J.C. Duke, Jr., E.G. Henneke, II, and K.L. Reifsnider, "Thermographic investigation of high–power ultrasonic heating in materials", Ultrasonic, Jul. 1981, pp. 159–165.

\* cited by examiner

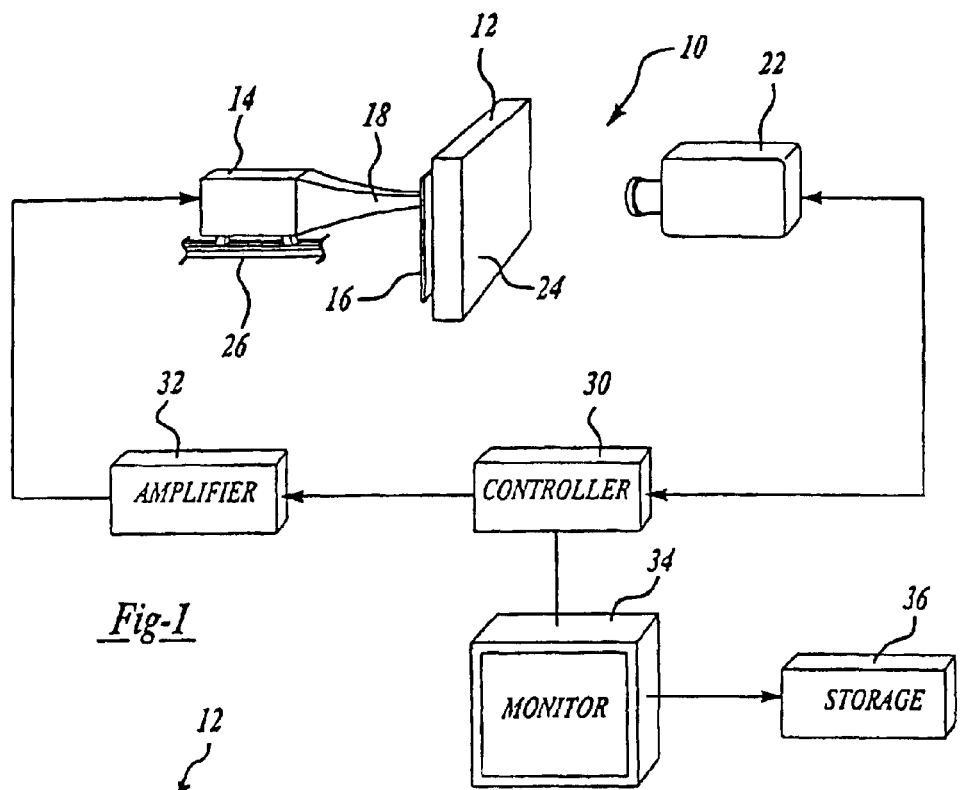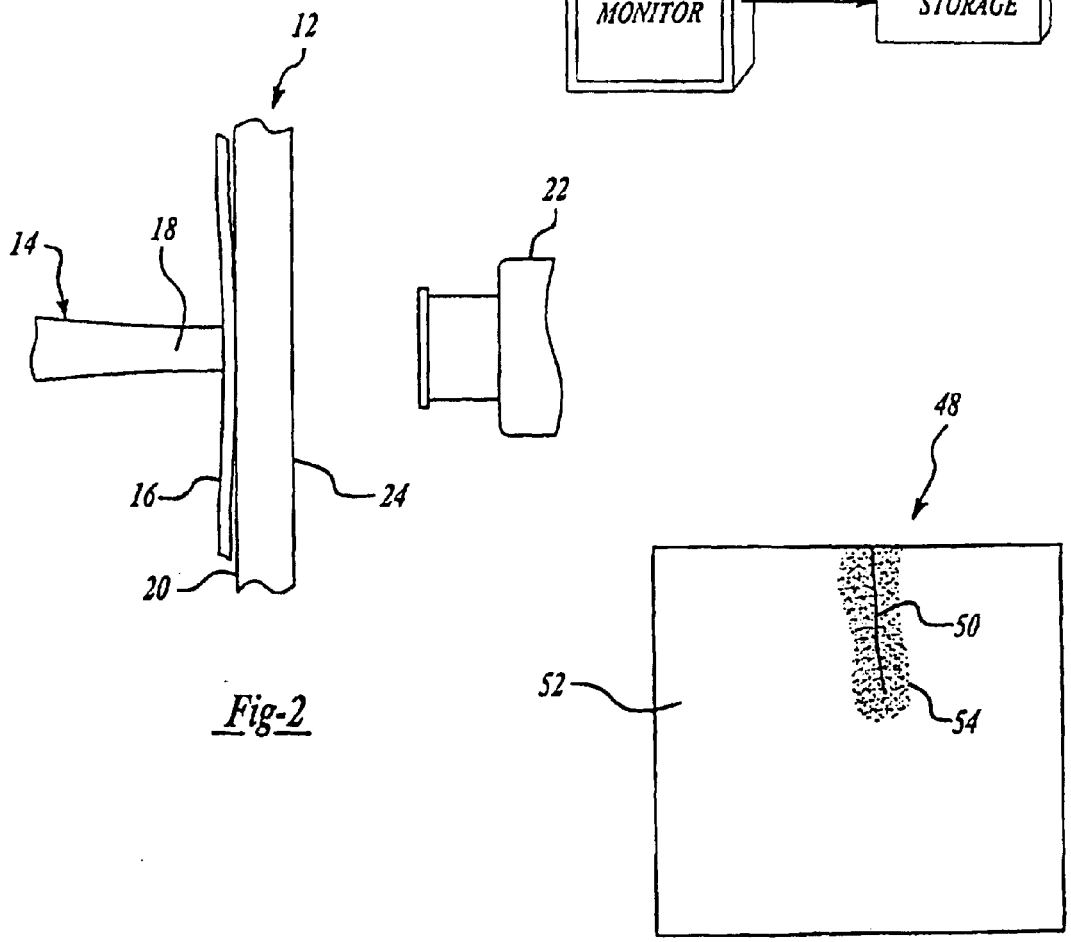

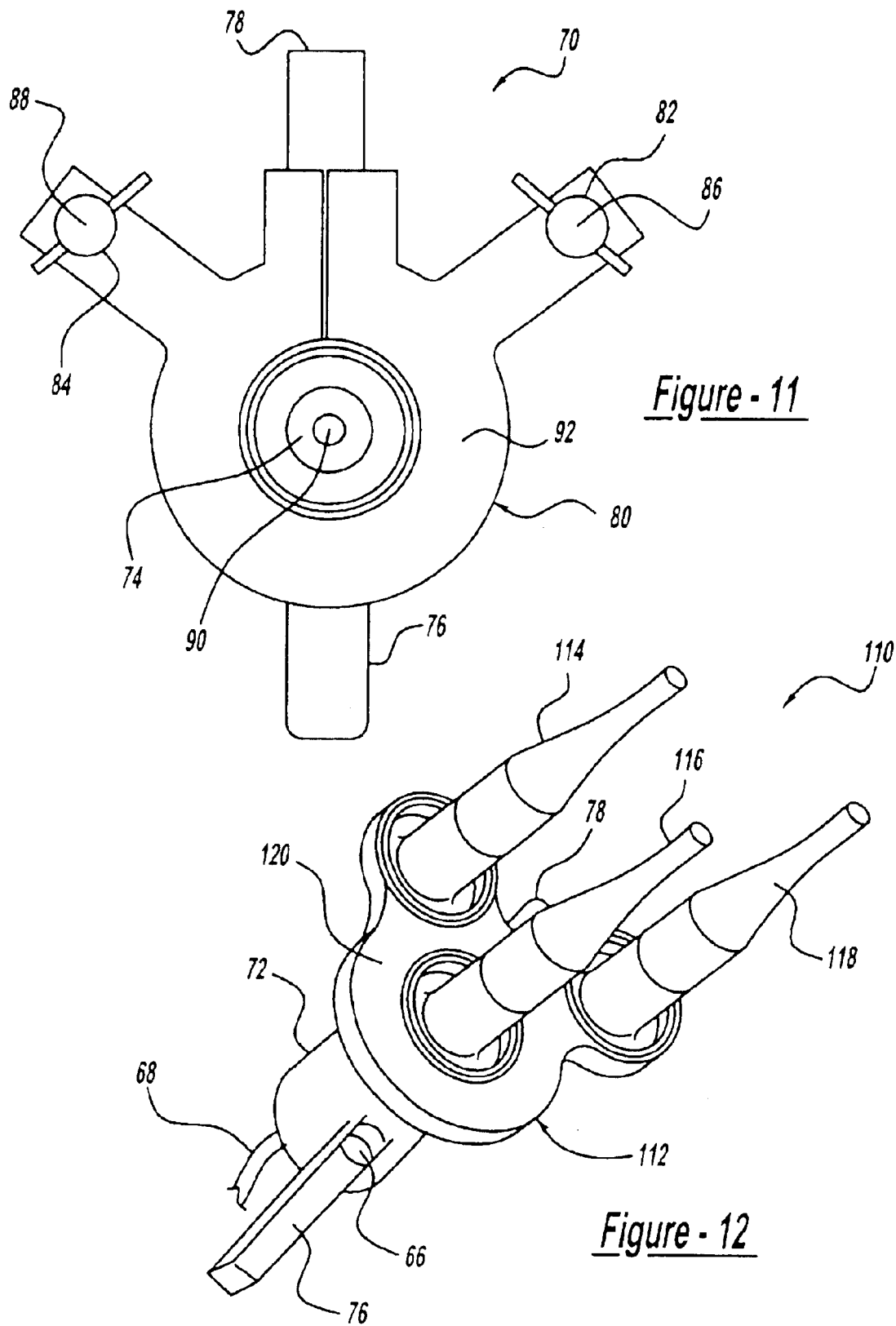

THERMAL IMAGING SYSTEM FOR DETECTING DEFECTS

CROSS-REFERENCE TO RELATED APPLICATION

This application is a continuation application of U.S. patent application Ser. No. 09/802,281, titled Hand-Held Sound Source Gun for Infrared Imaging of Sub-Surface Defects in Materials, filed Mar. 8, 2001, now U.S. Pat. No. 6,593,574 which is a continuation-in-part application of U.S. patent application Ser. No. 09/397,585, titled Infrared Imaging of Ultrasonically Excited Subsurface Defects in Materials, filed Sep. 16, 1999, now U.S. Pat. No. 6,236,049 issued May 22, 2001.

BACKGROUND OF THE INVENTION

1. Field of the Invention

This invention relates generally to a system and method for the detection of defects in a material and, more particularly, to a technique for coupling ultrasonic energy into a material to heat cracks and other defects that may exist in the material, and then thermally imaging the material to identify the defects by the heat radiating therefrom.

2. Discussion of the Related Art

Maintaining the structural integrity of certain components and structures is very important in many areas because of safety concerns and the like. Loss of structural integrity is typically caused by material defects, such as cracks, delaminations, disbonds, corrosion, inclusions, voids and the like, that may exist in the component or structure. For example, it is very important in the aviation industry that reliable techniques are available to examine the structural integrity of the aircraft skin and structural components of the aircraft to ensure that the aircraft does not suffer from structural failure when in flight. The structural integrity of turbine blades and rotors, and vehicle cylinder heads is also important in those industries. Therefore, techniques have been developed for the non-invasive and non-destructive analysis of different structural components and materials in various industries.

One known technique for non-invasive and non-destructive testing for material defects includes treating the structural component with a dye penetrant so that the dye enters any crack or defects that may be present in the material. The component is then cleaned, and the structure is treated with a powder that causes the dye remaining in the cracks to wick into the powder. An ultraviolet (UV) light source is used to inspect the material to observe locations on the component that fluoresces as a result of the dye. This technique has the disadvantage, however, that it is highly inspector intensive and dependent because the person inspecting for the fluorescence must be skilled. Additionally, the dye does not typically penetrate tightly closed cracks or cracks that are not on the surface.

A second known technique for inspecting a component for defects employs an electromagnetic coil to induce eddy currents in the component. The coil is moved around on the component, and the eddy current pattern changes at a crack or other defect. The complex impedance in the coil changes as the eddy current changes, which can be observed on an oscilloscope. This technique has the drawback that it is also very operator intensive, and also extremely slow and tedious.

Another known technique employs thermal imaging of the component to identify the defects. Typically, a heat source, such as a flash lamp or a heat gun, is used to direct a planar pulse of heat to the surface of the component. The material of the component absorbs the heat, and emits reflections in the infrared wavelengths. Certain types of defects will cause the surface temperature to cool at a different rate over the defects than for the surrounding areas. A thermal or infrared imaging camera is used to image the component and detect the resulting surface temperature variation. Although this technique has been successful for detecting disbonds and corrosion, it is ordinarily not successful for detecting vertical cracks in the material, that is, those cracks that are perpendicular to the surface. This is because a fatigue crack looks like a knife edge to the planar heat pulse, and therefore no, or minimal, reflections occur from the crack making the cracks hard or impossible to see in the thermal image.

Thermal imaging for detecting defects in a material has been extended to systems that employ ultrasonic excitation of the material to generate the heat. The article Rantala, J. et al, "Lock-in Thermography with Mechanical Loss Angle Heating at Ultrasonic Frequencies," Quantitative Infrared Thermography, Eurotherm Series 50, Edizioni ETS, Pisa 1997, pg 389–393 discloses such a technique. In this technique, ultrasonic excitation is used to cause the crack or defect to "light up" as a result of the ultrasonic field. Particularly, the ultrasonic waves cause the opposing edges of the crack to rub together causing the crack area to heat up. Because the undamaged part of the component is only minimally heated by the ultrasonic waves, the resulting thermal images of the material show the cracks as bright areas against a dark background field.

The transducer used in the ultrasonic thermal imaging technique referred to above makes a mechanical contact with the component being analyzed. However, it is difficult to couple high power ultrasonic energy into some materials, particularly in the case of metals. Significant improvements in this technique can be achieved by improving the coupling between the ultrasonic transducer and the component.

Additionally, the known ultrasonic thermal imaging technique employs complex signal processing, particularly vector lock-in, synchronous imaging. Vector lock-in imaging uses a periodically modulated ultrasonic source and includes a processing technique that synchronously averages successive image frames producing an in-phase image and a quadrature image both based on the periodicity of the source. This results in images that are synchronous with the periodicity and eliminates unsynchronous noise from the image. The periodicity of the image can also be induced by an external stimulus, such as a modulated laser beam, heat lamps, etc. The processor receives the frames of video images and stores them synchronously with the induced periodicity, and then averages the stored frames with subsequently received frames to remove the noise. U.S. Pat. No. 4,878,116 issued Oct. 31, 1989 issued to Thomas et al discloses this type of vector lock-in imaging.

U.S. Pat. No. 5,287,183 issued to Thomas et al Feb. 15, 1994 discloses a synchronous imaging technique that is a modification of the vector lock-in imaging disclosed in the '116 patent. Particularly, the imaging technique disclosed in the '183 patent extends the vector lock-in synchronous imaging technique to include a "box car" technique variation where the source is pulsed, and the images are synchronously averaged at various delay times following each pulse. The box car technique multiplies the video signal by zero except in several narrow time windows, referred to as gates, which are at a fixed time delay from the initiation of each ultrasonic pulse. The effect of these gates is to acquire several images corresponding to the states of component being imaged at the predetermined fixed delay times after the pulses. These different delay times are analogous to the different phases, represented by the sine and cosine functions of the periodic signal in the lock-in technique. During the acquisition of the gated images, the images corresponding to different delay times are combined arithmetically by pixel-by-pixel subtraction to suppress non-synchronous background effects.

The ultrasonic excitation thermal imaging technique has been successful for detecting cracks. However, this technique can be improved upon to detect smaller cracks, as well as tightly closed cracks, with much greater sensitivity. It is therefore an object of the present invention to provide a defect detection system that uses sound energy to detect subsurface defects in materials, and particularly such a system that employs a hand-held sound source.

SUMMARY OF THE INVENTION

In accordance with the teachings of the present invention, a system is disclosed for thermal imaging of ultrasonically excited subsurface defects in a structure. A sound source is coupled to the structure by a coupler, where the sound source transmits pulses of sound energy into the structure with minimum attenuation. A thermal imaging camera is used to image the structure when it is being excited by the sound energy. A control unit is used to control the operation of the sound source and the camera for timing purposes.

In one embodiment, the sound source is a hand-held sound source. The hand-held sound source provides a way of conveniently exciting many locations on a large structure, such as an aircraft fuselage. The sound source includes a transducer that is positioned against the structure at a desirable location. To prevent the transducer from "walking" on the structure when the pulses of sound energy are emitted, the source includes a pair of legs that are also positioned against the structure to define a plane in combination with the transducer. The length of each leg is adjustable relative to the length of the transducer so that the source can be used against irregular surfaces. The legs include a rubber tip to further prevent the transducer from slipping on the structure. In an alternate embodiment, the source includes three transducers that define a plane and act to stabilize the source against the structure.

Additional advantages and features of the present invention will become apparent from the following description and the appended claims when taken in conjunction with the accompanying drawings.

BRIEF DESCRIPTION OF THE DRAWINGS

FIG. 1 is a block diagram of an imaging system according to the invention;

FIG. 2 is a broken-away, side view of the transducer, specimen and camera of the imaging system shown in FIG. 1;

FIG. 6 is an image generated by the imaging system of the invention, showing a closed crack excited by ultrasonic energy;

FIG. 11 is a front view of the gun shown in FIG. 9;

FIG. 12 is a perspective view of a hand-held, sound source gun for exciting a structure, according to another embodiment of the present invention.

DETAILED DESCRIPTION OF THE EMBODIMENTS

Figure 3:
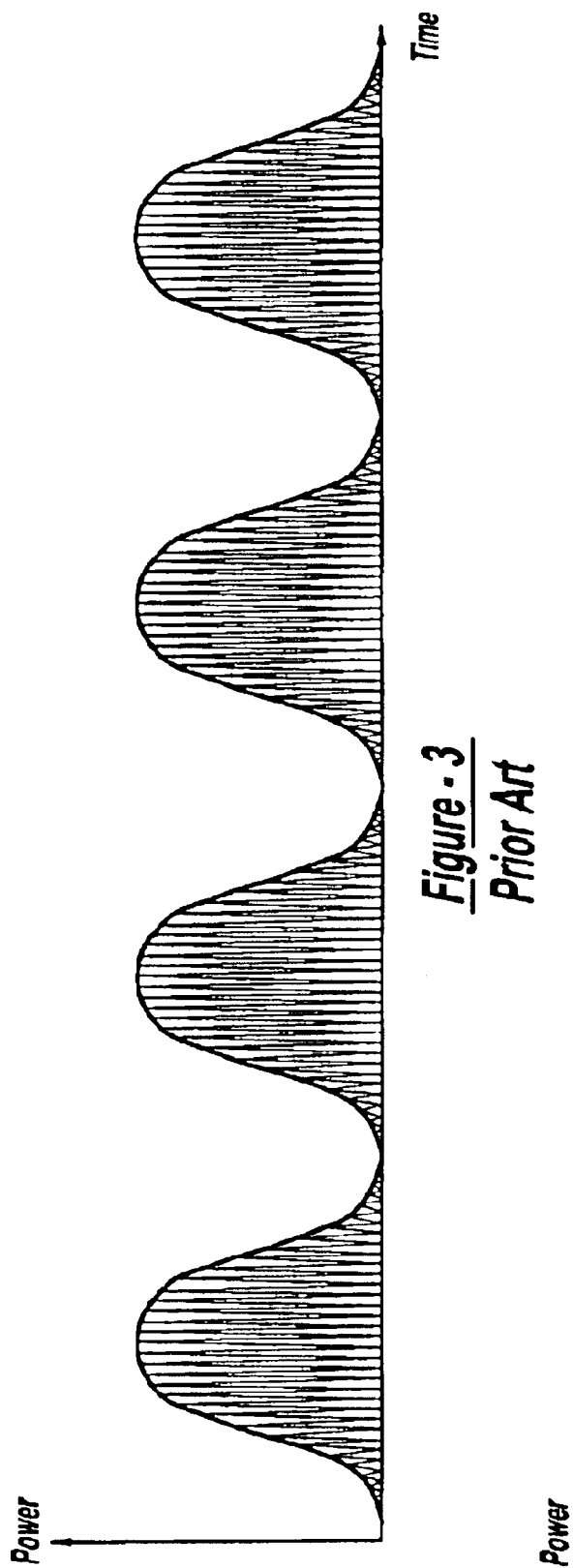
FIG. 3 is a graph with power on the vertical axis and time on the horizontal axis showing the ultrasonic signal used in the known thermal imaging techniques that employ vector lock-in synchronous imaging.

The following description of the embodiments of the invention directed to a thermal imaging system for detecting defects in a structure is merely exemplary in nature, and is in no way intended to limit the invention or its applications or uses.

FIG. 1 is a block diagram of an imaging system 10, according to an embodiment of the present invention. The imaging system 10 is being used to detect defects, such as cracks, corrosion, delaminations, disbonds, etc., in a specimen 12. The specimen 12 is intended to represent any structural component or material, such as an aircraft skin, that may include these types of defects. It is stressed that the specimen 12 does not need to be metal, but can be other material, such as ceramics, composites, etc. The system 10 includes an ultrasonic transducer 14 having a piezoelectric element that generates sonic or ultrasonic energy within a certain frequency band. The transducer 14 can be any transducer suitable for the purposes described herein, such as the Branson 900 MA ultrasonic transducer. In one embodiment, the ultrasonic transducer 14 generates a pulse of ultrasonic energy having a substantially constant amplitude at a frequency of about 20 kHz for a period of time of about ½ of a second and at a power level of about 1 kW. However, as will be appreciated by those skilled in the art, other ultrasonic frequencies, power levels and pulse durations can be used within the scope of the present invention.

The ultrasonic energy from the transducer 14 is coupled to the specimen 12 through a coupler 16. The coupler 16 is in mechanical contact with an end 18 of the transducer 14 and a front side 20 of the specimen 12. FIG. 2 is a broken-away, side view showing the transducer 14 in contact with the coupler 16 and the specimen 12. A support structure 26 is used to help maintain the transducer 14 in contact with the coupler 16. In one embodiment, the coupler 16 is a thin piece of a soft metal, such as copper, to effectively couple the ultrasonic energy into the specimen 12. Of course, other couplers consistent with the discussion herein can be used. For example, the coupler 16 can be a piece of cardboard or automotive gasket material. The coupler 16 can be any suitable piece of material that is typically softer than the end 18 of the transducer 14, and is malleable to be deformed against the end 18 of the transducer 14 and prevent the transducer 14 from bouncing or walking along the specimen 12. In one embodiment, the coupler 16 couples about 30 to 40 percent of the ultrasonic energy from the transducer 14 into the specimen 12. It is noted, however, that the coupler 16 may not be needed in certain applications, such as testing for defects in a composite.

A thermal imaging camera 22 is provided and spaced from a back side 24 of the specimen 12, and generates images of the side 24 of the specimen 12 in association with ultrasonic excitations of the specimen 12. The camera 22 can be spaced from the specimen 12 any suitable distance to provide images of as much of the specimen as desired in a single image. In other embodiments, the ultrasonic energy from transducer 14 and the image generated by the camera 22 can be provided at the same side of the specimen 12. The thermal camera 22 can be any camera suitable for the purposes described herein, such as the Galileo camera available from Raytheon. In one embodiment, the camera 22 senses infrared emissions in the 3–5 micron wavelength range, and generates images at 100 frames per second. The camera 22 includes a focal plane array having 256×256 InSb pixels to generate the resolution desirable. In one embodiment, the side 24 of the specimen 12 is painted black to provide better contrast for infrared imaging.

A controller 30 provides timing between the transducer 14 and the camera 22. The controller 30 can be any computer suitable for the purposes described herein. When the detection process is initiated, the controller 30 causes the camera 22 to begin taking sequential images of the specimen 12 at a predetermined rate. Once the sequence of images begins, the controller 30 sends a signal to an amplifier 32 that causes the amplifier 32 to send a pulse to the transducer 14 to generate the pulsed ultrasonic signal. The ultrasonic energy is in the form of a simple pulse at the frequency being used. It is not necessary to employ any type of vector lock-in or synchronous imaging techniques between the pulse of energy and the imaging, as is currently done in the prior art. However, such signal processing techniques can be used to further reduce noise. It is stressed that the frequencies and pulse time periods being described herein are by way of non-limiting examples, in that different ultrasonic frequencies, pulse times, input power, etc. will vary from system to system and specimen being tested. After the end of the pulse, the controller 30 instructs the camera 22 to stop taking images. The images generated by the camera 22 are sent to a monitor 34 that displays the images of the side 24 of the specimen 12. The images can then be sent to a storage device 36 to be viewed at another location if desirable.

The ultrasonic energy applied to the specimen 12 causes faces of the defects and cracks in the specimen 12 to rub against each other and create heat. This heat appears as bright spots in the images generated by the camera 22. Therefore, the system is very good at identifying very small tightly closed cracks. For those cracks that may be open, where the faces of the crack do not touch, the heating is generated at the stress concentration point at the crack tip. This point appears as a bright spot on the images indicating the end or tip of an open crack. The ultrasonic energy is effective to heat the crack or defect in the specimen 12 no matter what the orientation of the crack is relative to the energy pulse. The camera 22 takes an image of the surface 24 of the specimen 12, providing a visual indication of any crack in the specimen 12 no matter what the position of the crack within the thickness of the specimen 12.

The present invention provides improvements over the known ultrasonic and thermal imaging techniques because the ultrasonic pulses used to heat the cracks and defects are simple pulses having a substantially constant amplitude, and do not need to employ sinusoidal signal modulation as used in vector lock-in synchronous imaging. To illustrate this point, FIG. 3 shows a graph with power on the vertical axis and time on the horizontal axis depicting the waveform of the ultrasonic signal used in vector lock-in imaging. The ultrasonic signal is generated at a predetermined frequency, and modulated with a low frequency sinusoidal modulating wave that provides amplitude modulation at a predetermined modulation period. The ultrasonic frequency signal rises and falls in amplitude with the low frequency modulation wave. Typically, the ultrasonic excitation is performed over several seconds. The image generated by this imaging technique is not the actual image of the particular component being imaged, but is a difference image generated by the subtraction process of the synchronous imaging. A more detailed discussion of this type of vector lock-in synchronous imaging to reduce noise in these types of systems is discussed in the '116 patent.

Figure 4:
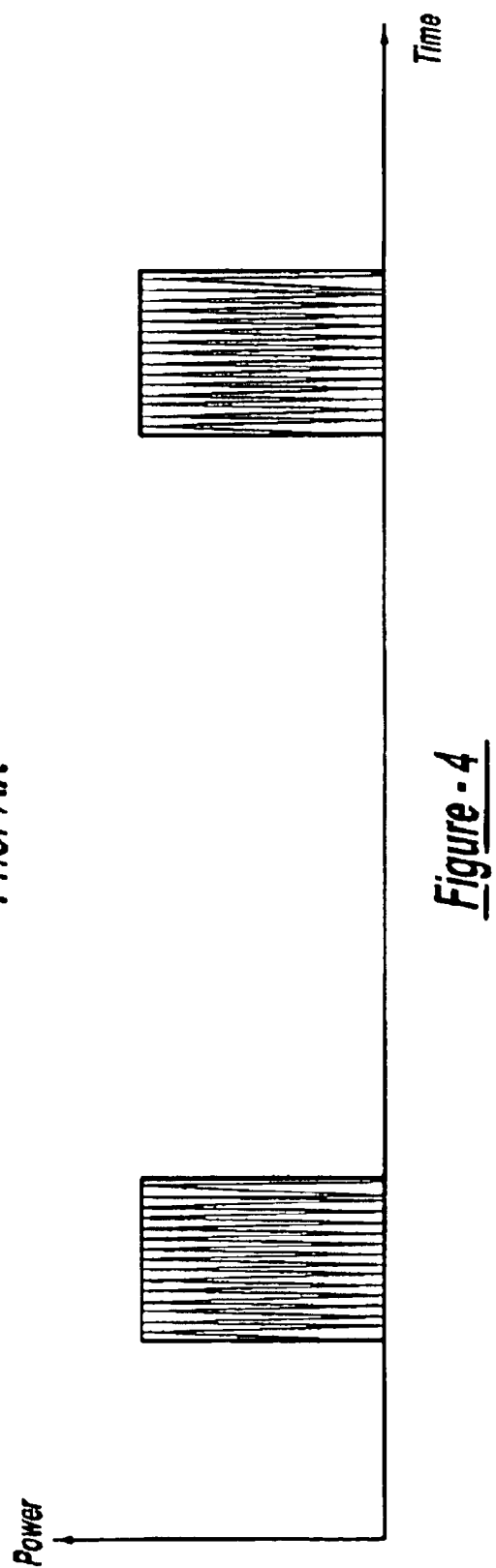
FIG. 4 is a graph with power on the vertical axis and time on the horizontal axis showing the pulsed ultrasonic signal used in the thermal imaging technique of the present invention.

FIG. 4 is a graph with power on the vertical axis and time on the horizontal axis showing the pulses used to provide the ultrasonic excitation in the present invention. The ultrasonic frequency signal within each pulse has substantially the same amplitude, and is not modulated by a lower frequency sinusoidal waveform. The images generated by the camera 22 are real images, and not difference images of the type generated in the vector lock-in synchronous imaging technique. This provides a significant improvement in image quality and control simplicity. Although one pulse is ordinarily sufficient, more than one pulse can be employed, separated in time by a predetermined time period, for signal averaging purposes to reduce noise. The technique of "box car" integration can be used as discussed in the '183 patent. In this technique, a gate is used in each time window to identify an image for each pulse, where the gate is at a certain fixed time delay from the beginning of the pulse. During the acquisition of the gated images, the images corresponding to different delay times are combined arithmetically to suppress non-synchronous background effects.

Figure 5A:
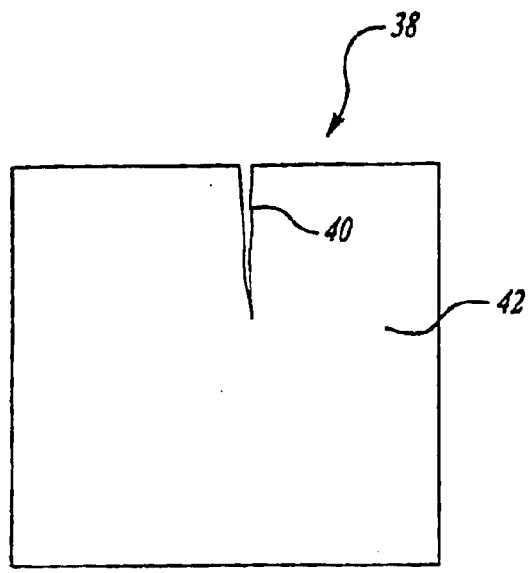
FIGS. 5(a)–5(d) show consecutive images at predetermined time intervals of an open crack in a specimen that has been ultrasonically excited and imaged by an imaging system of the present invention.
Figure 5B:
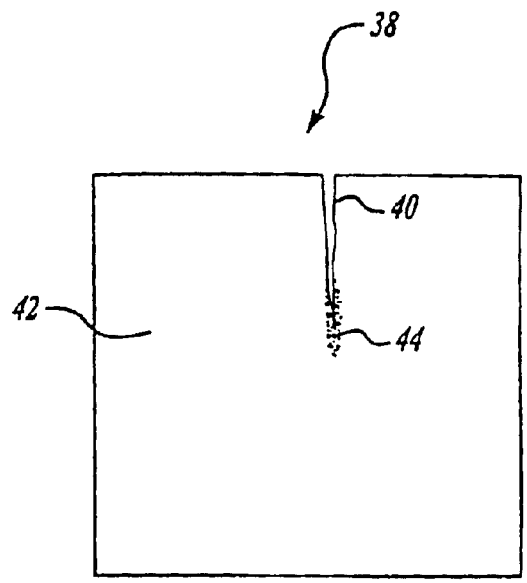
Figure 5C:
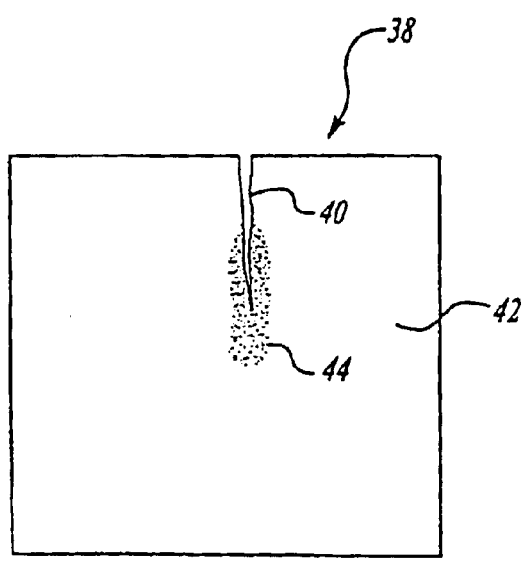
Figure 5D:
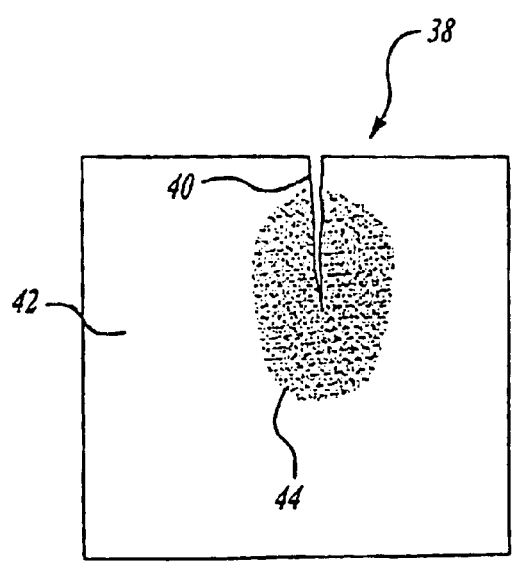

FIGS. 5(a)–5(d) show four sequential images 38 of an open fatigue crack 40 in a metal specimen 42. FIG. 5(a) shows the images 38 of the specimen 42 prior to the ultrasonic energy being applied. FIG. 5(b) shows the image 38 of the specimen 42 14 ms after the ultrasonic energy is applied. As is apparent, a light (higher temperature) spot 44 (sketched as a dark region) appears at the closed end of the crack 40, where the mechanical agitation causes the heating. FIGS. 5(c) and 5(d) show subsequent images 38 at time equal to 64 ms and time equal to 114 ms, respectively. The light spot 44 on the specimen 42 increases dramatically over this sequence, clearly indicating the location of the crack 40.

FIG. 6 shows an image 48 of a closed crack 50 in a specimen 52 after being energized by the ultrasonic pulse. In this embodiment, because the crack 50 is closed, the entire length of the crack 50 generates heat creating a light spot 54 along the entire length of the crack 50 and providing an indication of a closed crack. Because the ultrasonic energy is so effective in causing the closed crack 50 to heat up significantly relative to the background, very short closed cracks, for example on the order of $\frac{2}{3}$ mm, are readily ascertainable in the image 48.

Figure 7:
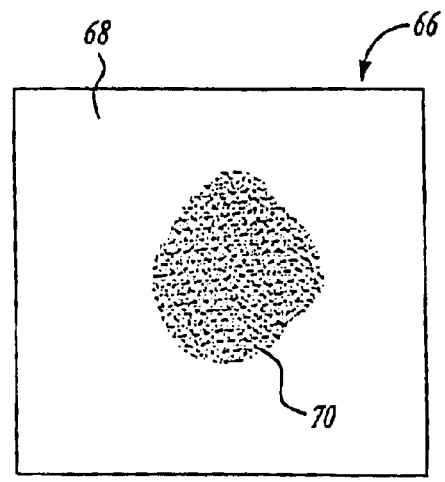
FIG. 7 is an image generated by the imaging system of the present invention, showing a delamination or disbond excited by the ultrasonic energy.

FIG. 7 shows an image 66 of a specimen 68. In this image, a light spot 70 is shown, and is intended to represent the type of image generated from the thermal energy that is created by ultrasonically exciting a delamination or disbond. The thermal imaging technique of the present invention is particularly useful in identifying "kissing" disbonds.

Figure 8:
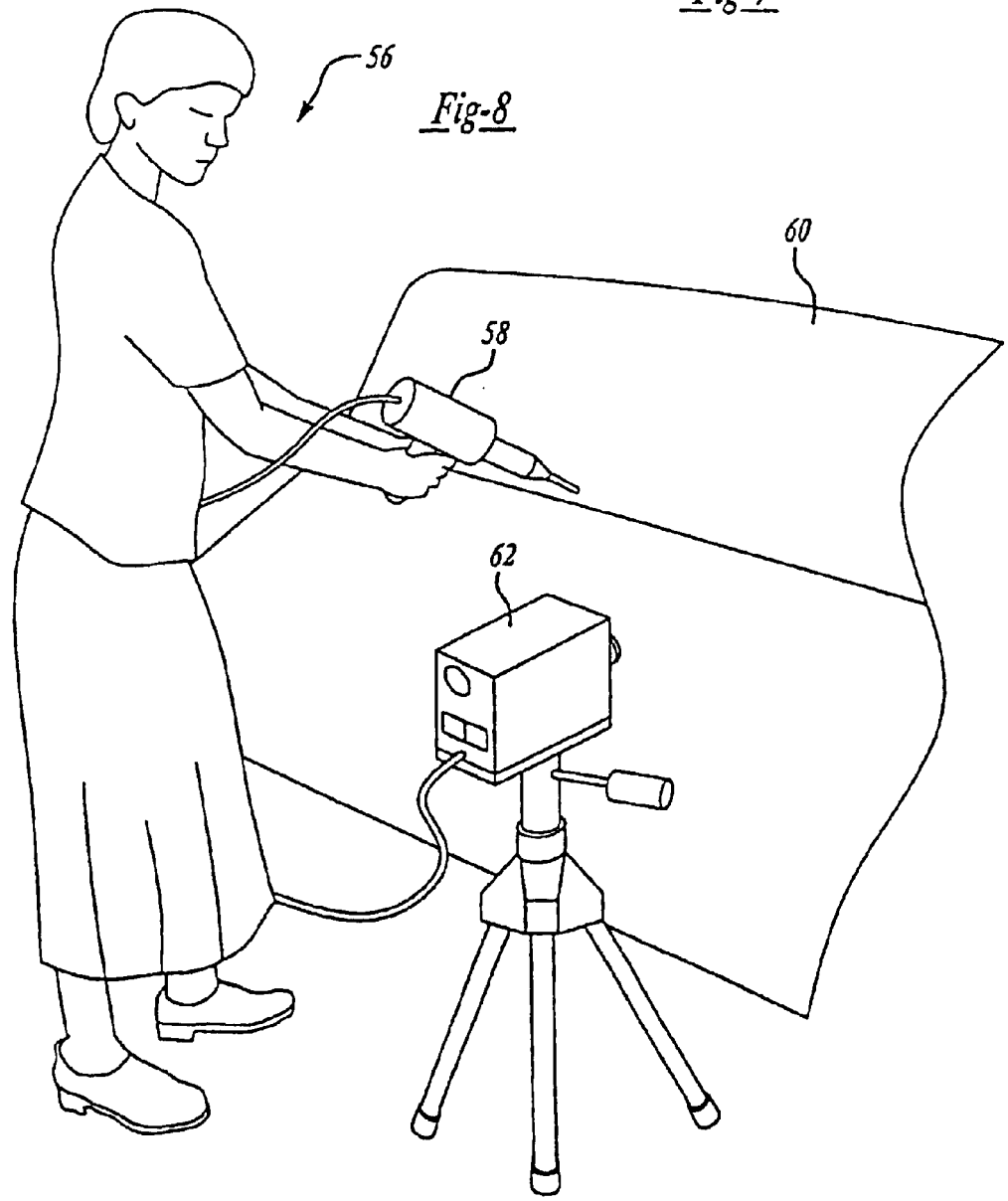
FIG. 8 is a perspective view of a person holding an ultrasonic transducer against an aircraft component, and using the imaging system of the present invention to detect cracks in the component.

FIG. 8 is a perspective view of an operator 56 holding a hand-held transducer 58 against a specimen 60, such as an aircraft fuselage. A thermal imaging camera 62 is directed towards the specimen 60 at a location that is separate from the point of contact of the transducer 58. FIG. 8 illustrates that the system according to the invention can be used in the field for testing such components.

For certain applications, the hand-held transducer 58 has limitations because it tends to "walk" or move on the structure when the pulse energy is emitted. Movement of the transducer 58 during the test reduces the coupling of the transducer 58 to the structure, thus reducing the amount of sound energy entering the structure and the quality of the resulting images. Thus, the ability to detect certain types of defects and possibly very small defects is limited.

Figure 9:
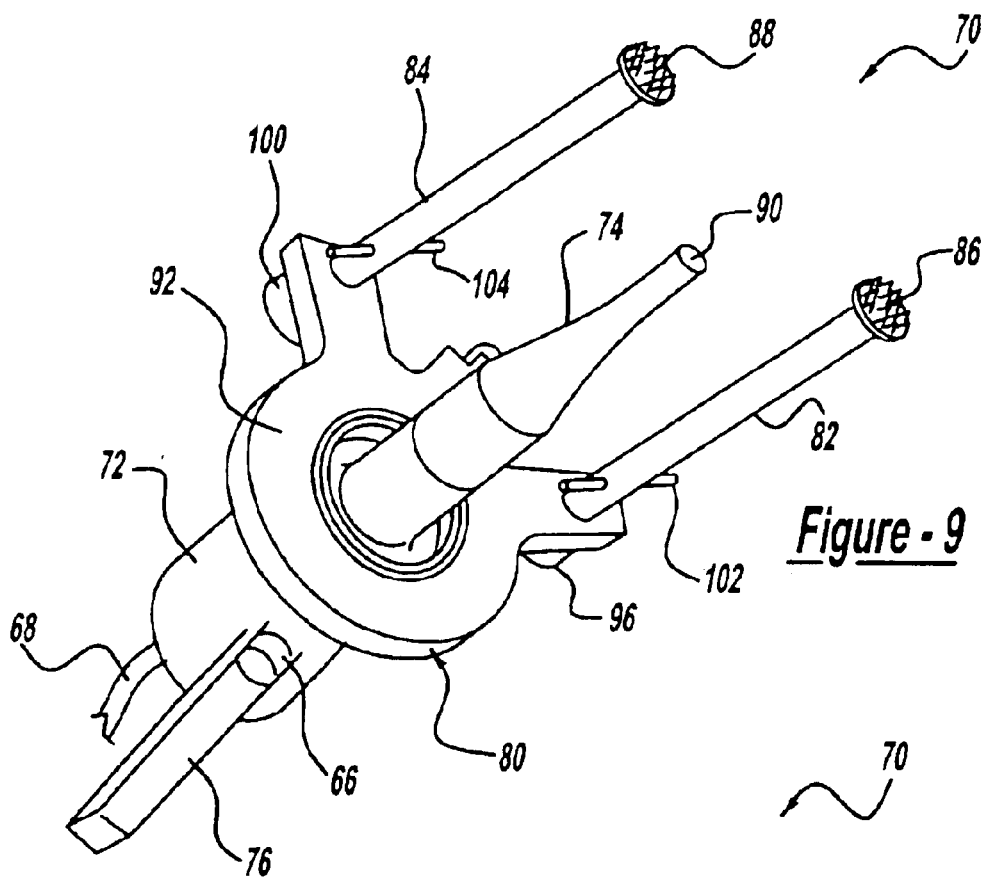
FIG. 9 is a perspective view of a hand-held, sound source gun for exciting a structure, according to an embodiment of the present invention.
Figure 10:
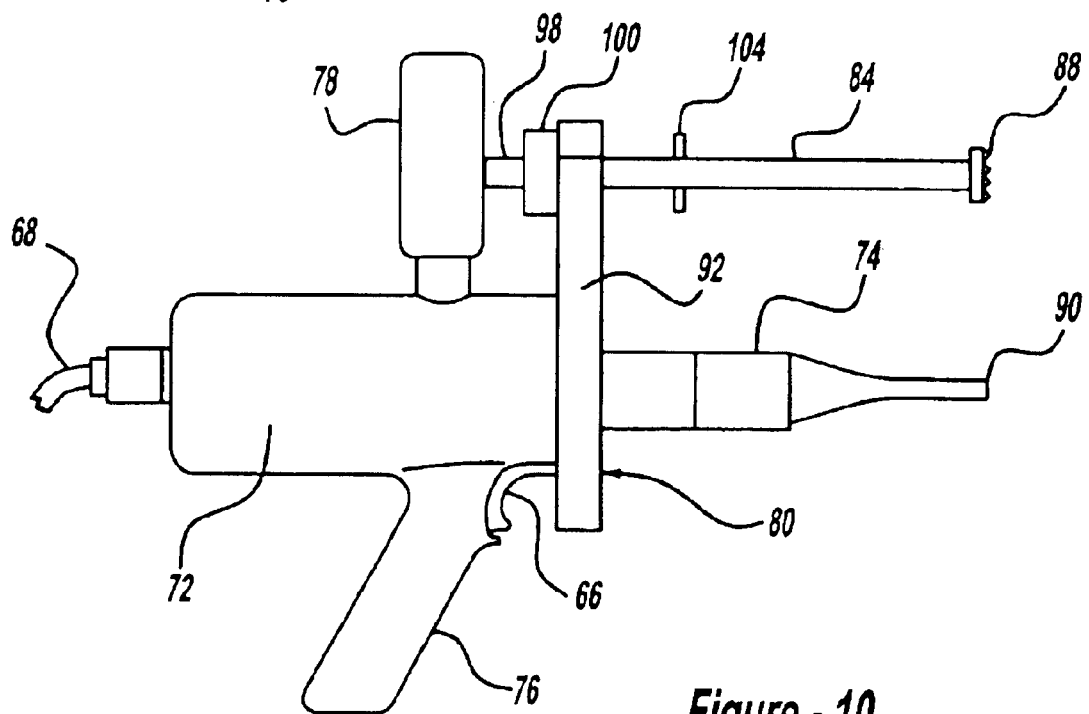
FIG. 10 is a side view of the gun shown in FIG. 9.

To overcome this limitation, the present invention proposes a modified hand-held, sound source gun 70 as depicted in FIGS. 9–11. The gun 70 includes a housing 72 that includes the components for generating the sound signal, as would be well understood to those skilled in the art. A transducer horn 74 is threadably mounted to one end of the housing 72 and extends therefrom. Thus, the horn 74 can be removed from the housing 72. One end of an electrical cable 68 is attached to the housing 72 at an end opposite from the horn 74, and an opposite end of the cable 68 is connected to the control unit, as discussed above. Further, a pistol-type grip 76 extends from a bottom of the housing 72, and a stabilizing grip 78 extends from a top of the housing 72 to allow an operator to firmly grip the gun 70 during testing. A trigger switch 66 on the grip 76 allows the operator to activate the sound source.

The gun 70 further includes a bracket assembly 80 clamped to an end of the housing 72 proximate the horn 74, as shown. The bracket assembly 80 can be clamped to the housing 72 in any suitable manner for the purposes described herein. The bracket assembly 80 includes a first leg 82 and a second leg 84 mounted thereto. The legs 82 and 84 are substantially parallel to the horn 74, and are about the same length. The bracket assembly 80 includes a base plate 92 that has a particular shape suitable to position the legs 82 and 84 a certain distance apart, as shown. The first leg 82 includes a rubber tip 86 and the second leg 84 includes a rubber tip 88 opposite the housing 72. The rubber tips 86 and 88 allow the gun 70 to be more firmly positioned against the structure to prevent slipping. The tips 86 and 88 can be made of other, non-slip materials, as would be appreciated by those skilled in the art. The operator places the tip 90 of the horn 74 and the tips 86 and 88 of the legs 82 and 84, respectively, against the structure being tested. The combination of the horn 74 and the legs 82 and 84 define a plane that prevents the horn 74 from moving when it is activated.

The first leg 82 also includes a tip 94 that is threadably attached to and extends through the bracket assembly 80 and is secured thereto by a lock nut 96. Likewise, the second leg 84 includes a tip 98 that is threadably attached to and extends through the bracket assembly 80 and is secured thereto by a lock nut 100. The leg 82 includes a pin 94 and the leg 84 includes a pin 96 that allow the legs 82 and 84 to be easily rotated. In this manner, the length of the legs 82 and 84 can be adjusted relative to the horn 74. This allows the gun 70 to be used against irregular surfaces.

Figure 13:
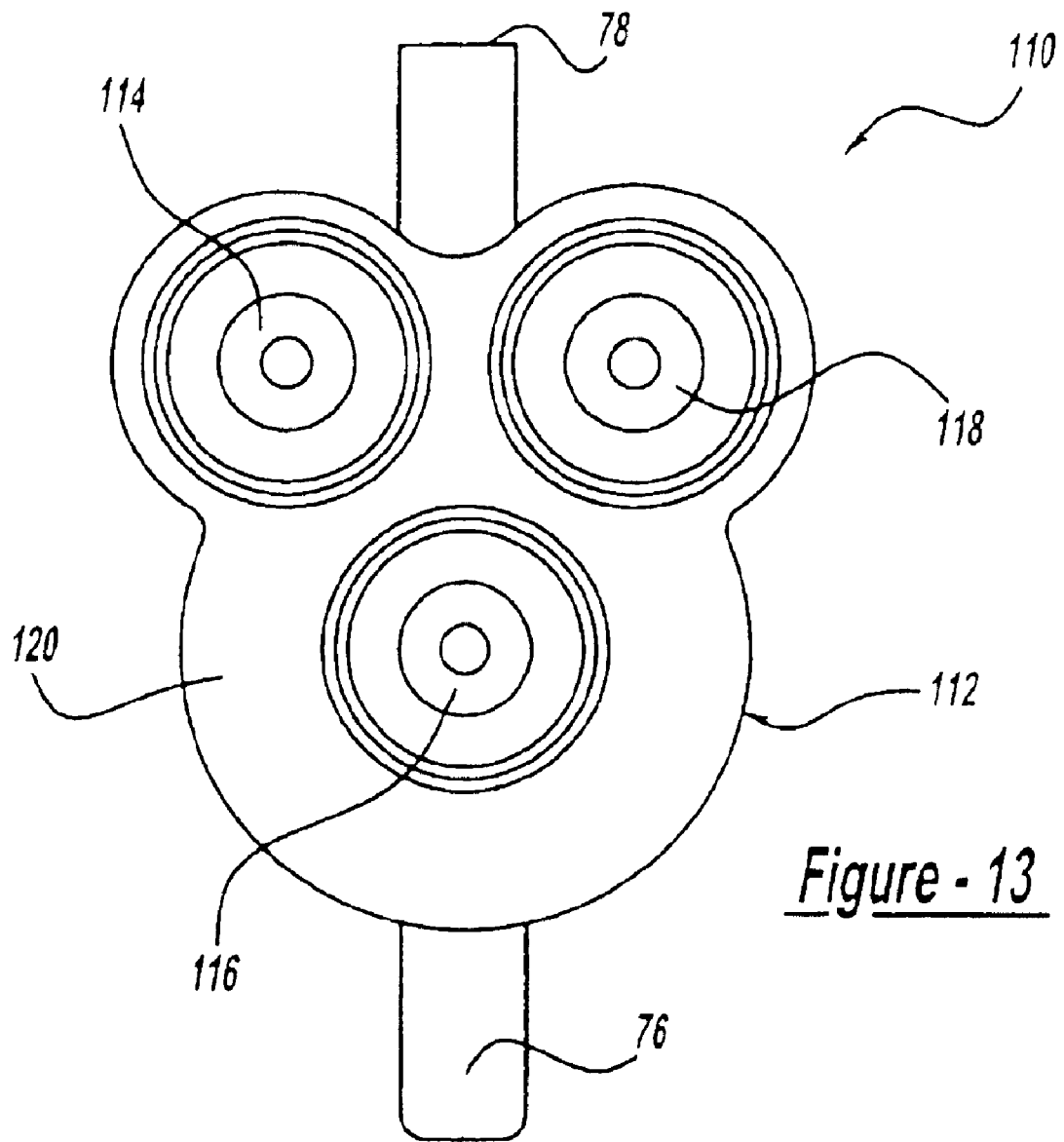
FIG. 13 is a front view of the gun shown in FIG. 12.

FIGS. 12 and 13 show a perspective view and a front view, respectively, of a hand-held gun 110 that is a modification of the gun 70, where like reference numerals identify the same components. As discussed above, the horn 74 is threaded into the housing 72 and can be removed therefrom. For the gun 110, the horn 74 and the bracket assembly 80 have been removed, and replaced with a horn structure 112. The structure 112 includes a threaded tip (not shown) that is threaded into the housing 72 in the same manner as the horn 74.

The structure 112 includes a base plate 120 and three horns 114, 116 and 118 symetrically disposed about the plate 120, as shown. The horns 114–118 are attached to the plate 120 by any suitable technique and can be integral therewith. The horns 114–118 provide the three leg foundation that defines a plane, and prevents the horns 114–118 from walking when the gun 110 is activated. The power from the sound generating components is distributed to the horns 114–118 evenly, which then enters the structure from three different locations.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A thermal imaging system for detecting defects in a structure, said system comprising:

a sound source;

a thermal imaging camera directed towards the structure and generating thermal images of the structure; and a controller electrically coupled to the sound source and the camera, said controller causing the sound source to transmit a series of sound pulses into the structure separated by a predetermined time period at a predetermined frequency, said controller causing the camera to generate sequential images of the structure, wherein vibrational energy from the pulses cause the defects in the structure to heat up and be visible in the images generated by the camera, and wherein the controller averages the images within a predetermined window in each pulse, where the window is provided at a same delay time in each pulse from when the pulse is initiated.

2. The system according to claim 1 further comprising a coupler positioned between and in contact with the structure and the sound source.

3. The system according to claim 2 wherein the coupler is malleable and is softer than an end of the sound source in contact with the coupler.

4. The system according to claim 2 wherein the coupler is a thin piece of metal.

5. The system according to claim 1 wherein the sound source is a hand-held sound source gun, said gun including a housing, at least one handle coupled to the housing, at least one sound transducer coupled to the housing, and a stabilizing structure coupled to the housing, said stabilizing structure including two elongated members, wherein the combination of the at least one transducer and the two separate elongated members provide three separate stabilizing points operable to be positioned against the structure to define a plane thereon.

6. The system according to claim 1 wherein the sound source emits a series of ultrasonic pulses.

7. A defect detection system for detecting defects in a structure, said system comprising:

a sound source for directing at least one pulse of a sound signal into the structure for a predetermined period of time;

a coupler positioned in contact with the structure and the sound source, said coupler being malleable and being softer than an end of the sound source in contact with the coupler;

a thermal camera directed towards the structure and generating thermal images of the structure when the sound source emits the sound signal; and a controller coupled to the sound source and the camera to provide timing signals therebetween, said controller being responsive to the images from the camera.

8. The system according to claim 7 wherein the coupler is a thin piece of metal.

9. The system according to claim 7 wherein the sound source is a hand-held sound source gun, said gun including a housing, at least one handle coupled to the housing, at least one sound transducer coupled to the housing, and a stabilizing structure coupled to the housing, said stabilizing structure including two elongated members, wherein the combination of the at least one transducer and the two separate elongated members provide three separate stabilizing points operable to be positioned against the structure to define a plane thereon.

10. The system according to claim 9 wherein each of the two elongated members includes an adjusting device, said adjusting device being operable to adjust the length of the elongated member relative to the at least one transducer.

11. The system according to claim 7 wherein the sound source emits a series of ultrasonic pulses.

12. A method of detecting defects in a structure, said method comprising:

providing a sound source;

providing a coupler in contact with an end of the sound source and the structure, said coupler being malleable and being softer than the end of the sound source;

emitting at least one pulse of a sound signal from the sound source into the structure to heat the defects; and generating a sequence of thermal images of the structure prior to, during and after the emission of the sound signal.

13. The method according to claim 12 wherein providing a sound source includes providing a hand-held sound source gun including a housing, at least one handle coupled to the housing, at least one sound transducer coupled to the housing, and a stabilizing structure coupled to the housing, said stabilizing structure including two elongated members, wherein the combination of the at least one transducer and the two separate elongated members provide three separate stabilizing points operable to be positioned against the structure to define a plane thereon.

14. The method according to claim 13 wherein providing a sound source includes providing the hand-held sound source gun where the two elongated members include an adjusting device that adjusts the length of the elongated member relative to the at least one transducer.

15. The method according to claim 12 wherein providing a coupler includes providing a metal coupler.

* * * * *